US005706830A

United States Patent [19]
Parker

[11] Patent Number: 5,706,830
[45] Date of Patent: Jan. 13, 1998

[54] LIQUID VENTILATOR SYSTEM AND USE THEREOF

[75] Inventor: James C. Parker, Mobile, Ala.

[73] Assignee: South Alabama Medical Science Foundation, Mobile, Ala.

[21] Appl. No.: 646,439

[22] Filed: May 6, 1996

[51] Int. Cl.$^6$ ........................................... A61M 15/00
[52] U.S. Cl. .............. 128/913; 128/203.12; 128/207.14; 128/207.15; 128/204.23
[58] Field of Search .................... 128/204.23, 203.12, 128/207.14, 207.15, 913, 910, 911, 912, 200.21, 204.21

[56] References Cited

U.S. PATENT DOCUMENTS

| | | | |
|---|---|---|---|
| 3,960,142 | 6/1976 | Elliott et al. | 128/204.23 |
| 4,248,221 | 2/1981 | Winnard | 128/207.15 |
| 4,346,702 | 8/1982 | Keebota | 128/912 |
| 4,598,706 | 7/1986 | Darowski et al. | 128/205.24 |
| 4,881,542 | 11/1989 | Schmidt et al. | 128/207.14 |
| 5,309,906 | 5/1994 | LaBombard | 128/911 |
| 5,315,992 | 5/1994 | Dalton | 128/207.15 |
| 5,335,650 | 8/1994 | Shaffer et al. | 128/913 |
| 5,437,272 | 8/1995 | Fuhrman | 128/913 |
| 5,438,982 | 8/1995 | MacIntyre | 128/207.14 |
| 5,492,109 | 2/1996 | Hirschl et al. | 128/913 |

FOREIGN PATENT DOCUMENTS

| | | | |
|---|---|---|---|
| 00664701 | 11/1982 | European Pat. Off. | 128/207.15 |
| 0858824 | 8/1981 | U.S.S.R. | 128/913 |
| WO 93/09833 | 5/1993 | WIPO . | |

OTHER PUBLICATIONS

Curtis, S.E., et al. *J. Appl. Physiol.* 68:2322–2328, 1990.
Hirschl, R.B., et al. *Crit. Care Med.* 23:157–163, 1995.
Hirschl, R.B.., et al. *Lancet* 346:1201–1202, 1995.
Koen, P.A., et al. *Pediatric Res.* 24:291–296, 1988.
Moskowitz, G.D., et al. *Journal of the Association for the Advancement of Medical Instrumentation* 5:273–278, 1971.
Ravenscraft, S.A., et al. *Am. Rev. Respir. Dis.* 148:345–351, 1993.
Shaffer, T.H., and Moskowitz, G.D., *J. Appl. Physiol.* 36:208–213, 1974.
Shaffer, T.H., et al. *Pediatric Pulmonology* 14:102–109, 1992.
Wolfson, M.R., et al. *J. Appl. Physiol.* 65(3): 1436–1443, 1988.
Wolfson, M.R., et al. *J. Appl. Physiol.* 72(3):1024–1031, 1992.
Shaffer, T.H., et al. In: *New Therapies for Neonatal-Respiratory Failure: A Physiologic Approach*, Eds. B.R. Boynton, W.A. Carlo, A.H. Jobe. Cambridge Univ. Press, Cambridge, UK, pp. 279–301, 1994.

*Primary Examiner*—Vincent Millin
*Assistant Examiner*—V. Srivastava
*Attorney, Agent, or Firm*—Jaeckle Fleischmann & Mugel, LLP

[57] ABSTRACT

The subject invention provides a liquid ventilator system which comprises a source of oxygenated liquid, an inspiratory conduit, a bifurcated bronchial tube, and a pump. The bifurcated bronchial tube has a left lumen for directing the flow of oxygenated liquid into the left primary bronchus of a subject, and a right lumen for directing the flow of oxygenated liquid into the right primary bronchus of a subject. The invention further provides a method for liquid ventilation of a subject using the system, as well as a method of increasing ventilation efficiency by continuous isovolumetric flow of oxygenated liquid into the bronchi of the subject.

11 Claims, 3 Drawing Sheets

LIQUID VENTILATOR SYSTEM AND USE THEREOF

FIELD OF THE INVENTION

The present invention relates to ventilator systems and, more particularly, to a liquid ventilator system using a bifurcated catheter to deliver liquid to the distal airways with an isovolumetric baseline flow throughout the ventilatory cycle to reduce dead space during ventilation.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The Adult Respiratory Distress Syndrome (ARDS) is the end result of numerous types of traumatic or septic insult, which result in severe impairment of gas exchange at the alveolar level (Petty and Ashbaugh 1971; Pingleton 1988). Pathologic features include alveolar edema with protein rich exudate, infiltration of inflammatory cells, sloughing of alveolar epithelium, vascular plugging, and regional atelectasis (Bachofen et al. 1979). A decrease in lung compliance and loss of surfactant function accompany the edema and inflammation (Petty and Ashbaugh 1971; Bachofen et al. 1979; Freenfield et al. 1964).

The Infant Respiratory Distress Syndrome (IRDS) also presents with regional atelectasis, edema and over-distended regions, but with more proliferative changes than in the adult (Obrodovich and Mellins 1985). IRDS accompanies premature birth prior to maturation of alveolar type II cells that produce endogenous surfactant (Parker 1993). Intratracheal instillation of artificial surfactant at birth has dramatically improved lung function and prognosis in premature births and reduced the need for ventilatory support (Jobe et al. 1987). However, premature births complicated with sepsis or cerebral bleeding may progress to IRDS, and both IRDS and ARDS result in high mortality rates (Petty and Ashbaugh 1971; Obrodovich and Mellins 1985; Northway et al. 1967).

It is now recognized that ventilatory support of respiratory distress may itself contribute to progression of the respiratory distress syndrome, because high inspired oxygen concentrations may lead to generation of cytotoxic oxygen free radicals, and high inspiratory pressures may cause mechanical damage to vessels and parenchyma (Freeman and Crapo 1982; Webb and Tiemey 1974). Experimental studies have shown that lung microvascular damage with resultant capillary leak of fluid and protein can occur at peak inflation pressures well below those required for lung rupture and air leak from the lung (Parker 1993). Parker et al. (1984) reported a direct relationship of pulmonary microvascular filtration coefficients in isolated dog lungs at peak inflation pressures higher than 42 cm $H_2O$. In addition, clearance of large solute molecules across pulmonary epithelium in sheep increased at peak pressures above 35 cm $H_2O$ (Egan et al. 1976). Increased pulmonary fluid and protein clearances have also been demonstrated after high peak airway pressures (Parker et al. 1990; Jobe et al. 1983).

Subsequent studies suggested that volume rather than pressure per se produces permeability increases in alveolar epithelium and capillary endothelium (Parker 1993; Parker et al. 1984), since damage to normal lungs does not occur at volumes below total lung capacity. Hernandez et al. (1989) showed that microvascular permeability increases due to high peak airway pressures could be reduced when lung volume was limited by an intact chest wall and could be completely prevented when maximal volume was limited by a rigid body cast. Limitation of volume expansion by a lower intrinsic lung compliance would explain the higher susceptibility to high inflation pressures of the lungs of younger animals, neonates, and premature animals compared to adults (Jobe et al. 1983; Adkins et al. 1991).

The increasing amounts of collagen and elastic tissue in maturing lungs undoubtedly accounts for the higher tolerance of inflation pressures (Parker 1993). However, a low lung compliance conferred by a reduced amount of functional surfactant does not protect the lung against pressure or volume induced injury. Inactivation of surfactant with detergent in rabbit lungs resulted in a marked decrease in lung compliance, but Coker et al. (1992) observed that capillary filtration coefficients increased in treated lungs at lower peak inflation pressures than normal lungs. Therefore, a heterogeneous distribution of tidal volume with high regional stresses can produce significant lung damage even though overall lung compliance is low (Parker 1993). The congenital lack of surfactant in premature infants and the inactivation of surfactant function by proteinaceous edema fluid in adult permeability pulmonary edema lead to a low lung compliance and susceptibility of lungs to regional injury during air ventilation (Jobe et al. 1985; Seeger et al. 1985).

A loss of parenchymal tensile strength due to lack of collagen (premature) or pre-existing disease processes also contributes to susceptibility to barotrauma. Hernandez et al. (1990) reported that a sub-threshold oleic acid dose combined with ventilation at 24 cm $H_2O$ peak pressure resulted in a tripling of the capillary filtration coefficient in rabbit lungs, although neither treatment alone resulted in injury. Woodring (1985) reported an 88% incidence of some interstitial air in ARDS patients ventilated with 40 cm $H_2O$ peak pressure, a pressure which is well tolerated by normal human lungs.

Thus, there is ample evidence that gas ventilation with high peak inspiratory pressures and volumes may obtain immediate benefits in gas exchange but result in lung damage that will compromise the eventual prognosis of the patient. Although surfactant replacement is sufficient to prevent IRDS in many premature infants, many respiratory failure situations occur in infants and adults in which artificial surfactant is not effective and ventilation may result in cumulative lung injury and ultimate deterioration of lung function (Pingleton 1988; Jobe and Ikegami 1987). Liquid ventilation may be a useful adjunct to treatment in these cases.

Liquid ventilation with perfluorocarbons (PFC) has emerged as a promising method of sustaining gas exchange without the volutrauma resulting from gas ventilation of lungs containing edema and/or a high gas-liquid surface tension (Parker 1993; Shaffer et al. 1994). Perfluorocarbons are inert liquids with a high oxygen carrying capacity, and ventilation with these liquids offers several physiologic advantages in injured lungs (Shaffer et al. 1994). In computer tomography studies, gas ventilation in edematous lungs tended to distribute to non-dependent regions of lung whereas fluorocarbon liquid distributed homogeneously throughout the lungs (Hirschl et al. 1994b). Morphometric studies indicate a greater alveolar volume, increased alveolar surface area, a decreased wall thickness, and a lack of hyaline membranes in injured lungs ventilated with liquid rather than gas (Wolfson et al. 1992). The absence of the air-liquid interface causes septal capillaries to bulge into the alveolar spaces and increases the capillary surface area to alveolar volume ratio in liquid filled lungs by about 30% for lung volumes above 50% total lung capacity (Gil et al. 1979). Since lung compliance is dependent on alveolar surface tension, injured perfluorocarbon filled lungs generally show a 3–4 fold increase in lung compliance (Hirschl et al. 1995b). These factors result in a markedly improved ventilation/perfusion (VA/Q) matching and gas exchange compared to gas ventilation (Hirschl et al. 1994b). Additional beneficial effects of liquid ventilation are recruitment of atelectatic lung regions, a lavaging action which tends to remove edema fluid and debris (Wolfson et al. 1992), and an inhibitory effect on oxygen free radical production by inflammatory cells (Hirschl et al. 1995b; Smith et al. 1995).

Ventilation with PFC liquids has been used in animals models of lung injury and in patients with respiratory distress (Shaffer et al. 1994). Lungs can be ventilated either by using a total liquid filled lung or by partial liquid ventilation, where the lung is partially filled with liquid as gas ventilation is instituted. Leach et al. (1995) compared partial liquid ventilation to conventional mechanical gas ventilation with or without exogenous surfactant in premature lambs in respiratory distress. Five hour survival was markedly improved with partial liquid ventilation, lung compliance increased 4–5 fold, arterial $PO_2$ increased 6–7 fold, and lower mean airway pressures were attained using partial liquid ventilation. Exogenous surfactants were not inactivated by PFC liquids, but they did not further decrease surface tension in liquid filled lungs. Premature baboons (Sekins et al. 1994) and monkeys (Jackson et al. 1940) in respiratory distress tolerated partial liquid ventilation for 4 days with return of pulmonary function to near normal.

Liquid ventilation has also been applied to several adult animal models of lung injury with striking beneficial effects on lung function. In oleic acid injured sheep studies, where conventional and liquid ventilation were compared, liquid ventilation resulted in a 2–2.8 fold increase in lung compliance, a 6–7 fold increase in arterial $PO_2$, a significant decrease in arterial $PCO_2$, a 56–66% decrease in shunt flow, and reduced requirements for extracorporeal membrane oxygenation compared to gas ventilated sheep (Hernandez et al. 1990; Hirschl et al. 1995c; Hirschl et al. 1994b; Hirschl et al. 1995d). A marked decrease in intra-alveolar hemorrhage, alveolar exudate, and inflammation was also present with liquid compared to conventional gas ventilation. Similar improvements in lung compliance, arterial $PO_2$ and $PCO_2$, and VA/Q matching were obtained in oleic acid injured cats on liquid compared to gas ventilation (Hirschl et al. 1993). Liquid ventilation started immediately after gastric aspiration in newborn piglets prevented the histologic damage and gas-exchange abnormalities that developed with gas ventilation (Nesti et al. 1994).

Hirschl et al. (1995b) recently reported a study of partial liquid ventilation in human neonates, children, and adults who were in severe respiratory failure and being treated by extracorporeal membrane oxygenation. Eleven of 19 patients survived at 48 h of partial LV, which resulted in a 20% decrease in the alveolar-arterial $PO_2$ gradient and a 61% increase in static lung compliance. Although complications occurred in several patients, and the complexity of the cases prevented firm conclusions as to beneficial effects on prognosis, the patients tolerated the LV procedure well. Previous studies of alternating liquid with gas ventilation in premature human infants indicated that liquid ventilation was well tolerated and in some cases resulted in an improvement in lung function (Greenspan et al. 1989; Greenspan et al. 1990). However, the optimal liquid ventilation methods and most appropriate clinical applications require further investigations.

While liquid ventilation offers promise for minimal mechanical damage to the lung, there are aspects of fluid mechanics that tend to limit its effectiveness for gas exchange. These limitations occur because the PFC liquid is 100-fold more viscous and 1000-fold more dense than air, and $CO_2$ diffuses through PFC liquid 2500 times slower than air (Shaffer et al. 1994). Due to the high viscosity and density, maximal expiratory flow rates are 20 times less than that for air and are lung volume dependent below 50% of vital capacity (Schoenfish and Kylstra 1973). In addition, diffusional dead space for $CO_2$ is time dependent since dead space is reduced if ample time is allowed for diffusion (Koen et al. 1988; Schoenfish and Kylstra 1973). Therefore, $CO_2$ elimination is limited at low ventilation frequencies by the alveolar ventilation rate and at higher frequencies by the slow diffusion rate. Koen et al. (1988) found that the $CO_2$ elimination rate increases sharply with frequency to reach a peak at 3–5 breaths/min in cats but decreased at higher frequencies. Arterial oxygenation is subject to the same limitation but could be improved by increasing the $F_1O_2$ of inspired liquid. The high density of PFC liquids also leads to reductions in cardiac output compared to gas ventilation even though vertical gradients in blood flow become more homogenous (Lowe and Shaffer 1986).

A need continues to exist for improved liquid and/or partial liquid ventilation techniques which overcome the problems associated with conventional gas ventilation, while at the same time improving the effectiveness of liquid and/or partial liquid ventilation.

SUMMARY OF THE INVENTION

To this end, the subject invention provides a liquid ventilator which comprises a source of oxygenated liquid, an inspiratory conduit, a bifurcated bronchial tube, and a pump. The inspiratory conduit has a first end connected to the source of oxygenated liquid, and a second end which connects to the bifurcated bronchial tube. The bifurcated bronchial tube has a left lumen for directing the flow of oxygenated liquid into the left primary bronchus of a subject, and a right lumen for directing the flow of oxygenated liquid into the right primary bronchus of the subject. The pump is used to pump the oxygenated liquid from the source through the inspiratory conduit to the bifurcated bronchial tube, and thereby to the left and right primary bronchi.

The invention further provides a method for liquid ventilation of a subject. The method comprises inserting a bifurcated bronchial tube into a subject, and providing a flow of oxygenated liquid into the bifurcated bronchial tube, thereby ventilating the subject. The bifurcated bronchial tube is as described above.

The liquid ventilator and method as so described reduce dead space volume within the subject and therefore increase the efficiency of the ventilation.

The invention still further provides a method for increasing ventilation efficiency by continuous isovolumetric flow of oxygenated liquid into the bronchi of the subject.

BRIEF DESCRIPTION OF THE DRAWINGS

These and other features and advantages of this invention will be evident from the following detailed description of preferred embodiments when read in conjunction with the accompanying drawings in which:

FIG. 2 (A–C) shows the pattern of liquid ventilation and pump flow rates.

DETAILED DESCRIPTION OF THE INVENTION

Figure 1:
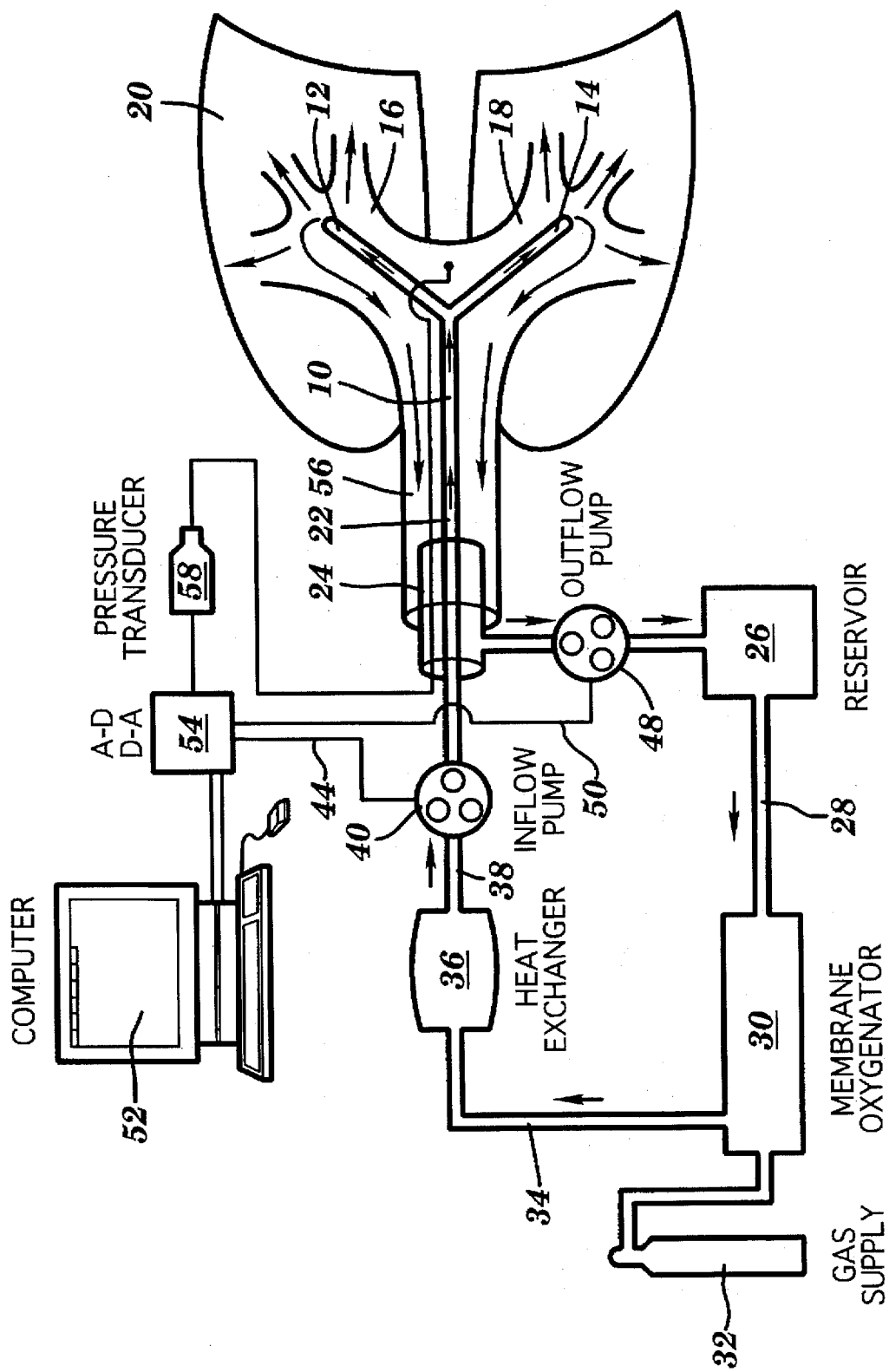
FIG. 1 is a diagram of a liquid ventilator system according to one embodiment of the subject invention.

The main components of a preferred embodiment of the subject invention are depicted in FIG. 1.

Referring to FIG. 1, the lungs 20 of a patient to be ventilated are shown. Respiration (gas exchange) within the lungs occurs at the alveoli, which are the termination points of the respiratory tree. The subject invention provides oxygenated liquid at the left primary bronchus 16 and the right primary bronchus 18 portions of the respiratory tree. As shown, the bifurcated bronchial tube 10 has a left lumen 12 which directs the flow of oxygenated liquid into the left primary bronchus 16, and a right lumen 14 which directs the flow of oxygenated liquid into the right primary bronchus 18. As further shown, the bifurcated bronchial tube 10 is a double lumen tube, with an inner lumen 22 for providing the flow of oxygenated liquid into the lungs, and an outer lumen 24 for removing de-oxygenated liquid from the lungs (see arrows which indicate direction of the flow of liquid).

The provision of the oxygenated liquid directly to the primary bronchi reduces the dead space volume normally associated with ventilation. More particularly, known endotracheal tubes for ventilation terminate within the trachea 56, leaving dead space from the trachea to the primary bronchi. By removing this dead space, a greater volume of inspiratory liquid is oxygenated, thereby increasing ventilation efficiency.

Referring again to FIG. 1, a reservoir 26 of liquid is provided, which connects via channel 28 to a membrane oxygenator 30. A gas supply 32 (i.e. oxygen supply) is connected to membrane oxygenator 30 so that the oxygen is perfused through the liquid from the reservoir 26. The oxygenated liquid then travels through channel 34 to the heat exchanger 36. The purpose of the heat exchanger 36 is to ensure that the oxygenated liquid is of the proper temperature before it is introduced into the lungs of the patient. From the heat exchanger 36, the oxygenated liquid travels through channel 38 to inflow pump 40 which then pumps the oxygenated liquid into the bifurcated bronchial tube 10. The inflow pump 40 works in combination with the outflow pump 48, under control of the computer 52. The computer 52 can be programmed to regulate the parameters of inspiration/expiration during the liquid ventilation. As shown in FIG. 1, the inflow pump 40 is connected to the computer 52 through connector 44 via the A-D board 54. Likewise, the outflow pump 48 is connected to the computer 52 through connector 50 also via the A-D board 54.

The liquid ventilator system as shown in FIG. 1 further includes a pressure transducer 58 which senses airway liquid pressure and relays that information through the A-D board 54 to the computer 52.

Having thus described the liquid ventilator system according to the subject invention, the system can be used to deliver a tidal volume of oxygenated liquid, together with a slow isovolumetric baseline flow which is maintained throughout the ventilatory cycle. This method prevents the conducting airway (i.e. the trachea) dead space liquid, which contains a high $CO_2$ and low $O_2$ content, from re-entering the alveoli on the next breath. Isovolumetric perfusion likely also exchanges gases independent of dead space effects, so gas exchange will be enhanced in spite of the high viscosity and low gas diffusion rates which inherently limit gas exchange during liquid ventilation at high frequencies.

The method uses a bronchial tube system for liquid infusion, a Basic language program for control of inflow and outflow pumps, and a pressure limiting sensor for maintaining safe lung fluid volumes and pressures. A heat exchanger and membrane oxygenator are arranged in series with the pumps in a fashion similar to previous liquid ventilators (Koen et al. 1988; Hirschl et al. 1995a; Moskowitz et al. 1971; Shaffer and Moskowitz 1974; Curtis et al. 1990). The control algorithm, pumps and oxygenator can be incorporated in a single microprocessor controlled unit.

The method of the subject invention improves the maximal $CO_2$ and $O_2$ exchange rates within the constraints of the high viscosity and low diffusion rates presented by PFC liquids. The ventilation system delivers a tidal volume of oxygenated liquid directly to distal airways so that alveoli are not filled with hypoxic dead space liquid on inspiration. A continuous isovolumetric replacement of dead space liquid with oxygenated liquid removes some hypoxic alveoli during inspiration, and some alveolar liquid is continuously exchanged with oxygenated liquid throughout the respiratory cycle resulting in a higher alveolar $PO_2$ and lower alveolar $PCO_2$ during inspiration. This in turn increases both the partial pressure gradients during gas diffusion and the gas exchange rates.

The method of liquid ventilation has many clinical uses. Promising clinical applications for liquid ventilation are in pediatric patients, including the ventilation of very low birth rate premature infants (500–1000 gm). While exogenous surfactant has increased survival rates of these infants, many experience severe crippling chronic lung disease after ventilatory support. Liquid ventilation may offer advantages in long term prognosis in this group of infants (Shaffer et al. 1983). Meconium aspiration pneumonia results in small airway obstruction and surfactant inactivation which may require extracorporeal oxygenation. The ability of liquid ventilation to lavage alveolar fluid and increase lung compliance indicate a beneficial application in such cases (Shaffer et al. 1984). Liquid ventilation may offer a treatment for lethal congenital diaphragmatic hernia with underdeveloped lungs (Cadenas et al. 1995). In adult patients, liquid ventilation may reduce mortality and long-term morbidity of the Adult Respiratory Distress Syndrome (Hirschl et al. 1995c). It may also serve as an adjunct to radiologic airway imaging and enhance detection of cancer and other pulmonary abnormalities (Thomas et al. 1986), serve as a route for administration of drugs, control body temperature, and prevent ischemia-reperfusion injury in lungs used for transplant (Shaffer et al. 1994). The very recent demonstration that partial liquid ventilation is well tolerated in neonates, children and adults in respiratory distress, suggest that an improved gas exchange efficiency would allow use of liquid ventilation as a less invasive and more economical alternative to extracorporeal membrane oxygenation.

EXAMPLE I

Liquid ventilator components and catheter. The liquid ventilation system consists of two voltage controlled roller pumps (Masterflex 7520, Cole-Palmer Inst., Co., Vernon Hills, Ill.) controlled by a digital computer (Gateway, Sioux Falls, S. Dak.) through a A-D/D-A interface board (DT2801, Data Translation, Marlborough, Mass.). As shown in FIG. 1, the circuit contains a heat exchanger (Avecor, Plymouth, Minn.), membrane oxygenator (Science Medical Life Systems), and a perfluorocarbon (PFC) reservoir. A bifurcating bronchial tube for distal delivery of oxygenated PFC liquid is placed in the airways. Tube diameter can be minimized by using high inflow pump pressures. A pressure transducer (Cobe Inst. Co.) senses airway liquid pressure which is relayed through the A-D board to the computer.

EXAMPLE II

Figure 2A:
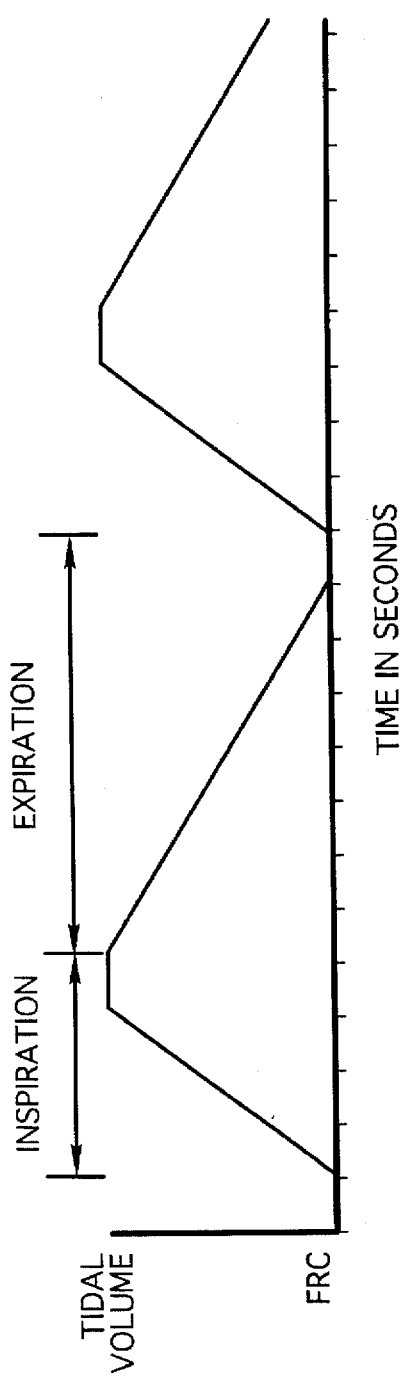
FIG. 2A represents tidal volume.
Figure 2B:
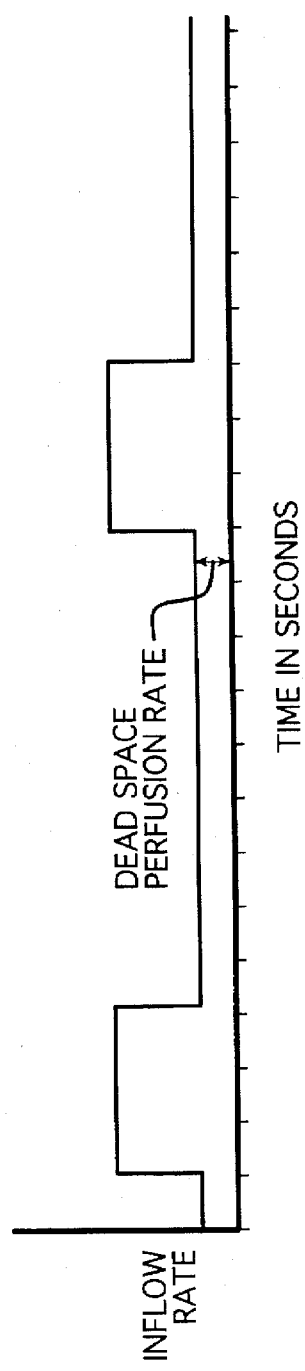
FIG. 2B represents inflow rate.
Figure 2C:
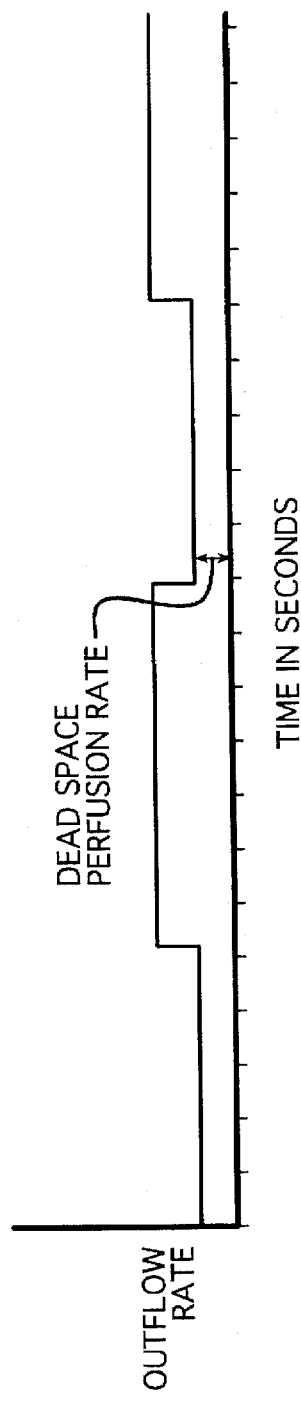
FIG. 2C represents outflow rate.

Ventilator pattern generation. FIG. 2 shows the pattern of ventilation generated by the inflow and outflow pumps. A Basic language program can be developed for controlling pump cycle time and flow rates. The distal airway liquid pressure will be maintained within predetermined limits by feed-back control of liquid inflow rates. A continuous isovolumetric flow rate is maintained throughout the ventilating cycle. Nominal ventilatory settings will be a tidal volume of 15 ml/kg body weight, a rate of 5 breaths/min with respective inspiration and expiration times of 4 s and 8 s. A nominal isovolumetric inflow and outflow perfusion rate of 25 ml/min/kg is maintained throughout the tidal volume by cycling of inflow and outflow pumps as shown in FIG. 2.

EXAMPLE III

Figure 3:
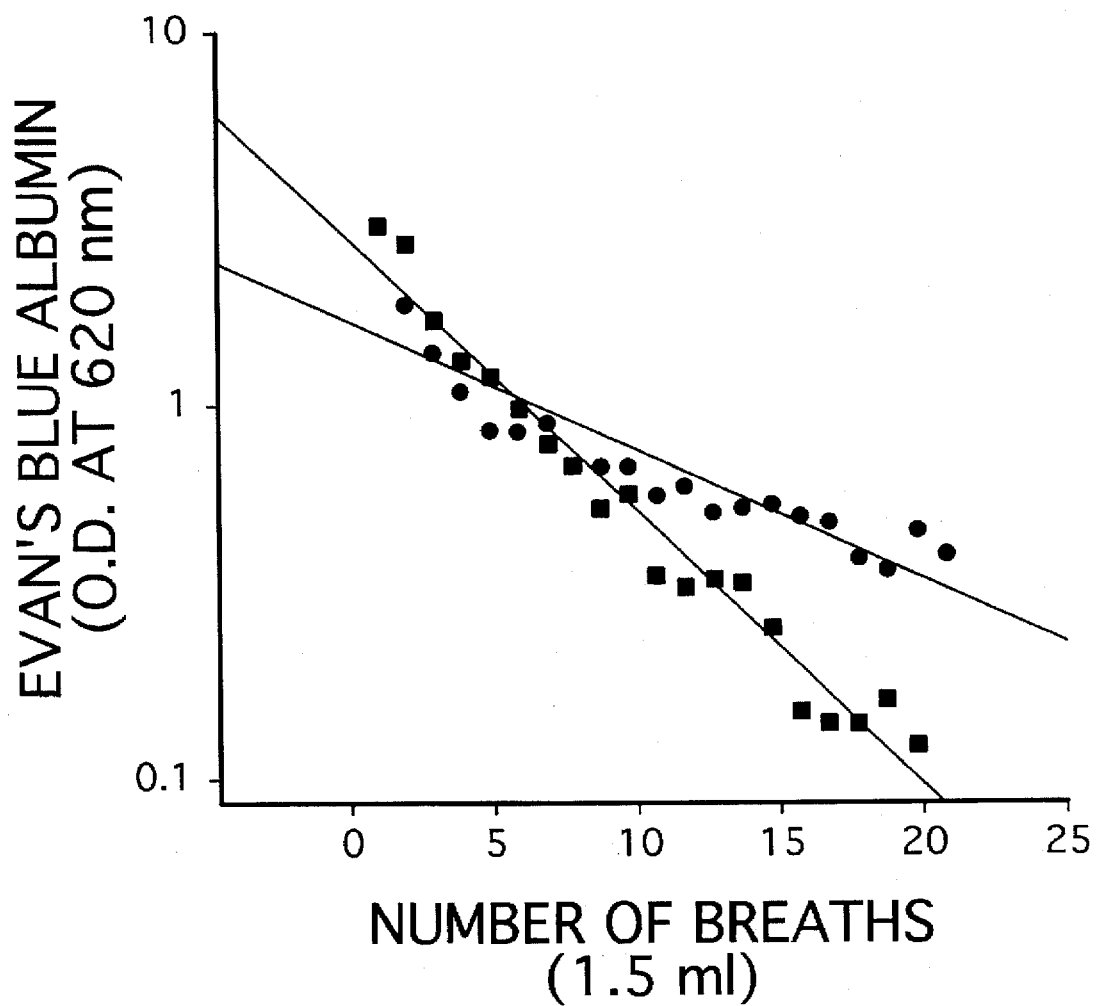
FIG. 3 shows the greater clearance rate (K) using the distal-perfused tidal ventilation according to one embodiment of the subject invention.

FIG. 3 shows a comparison of the wash-out rates of Evans Blue labelled albumin from rabbit lungs using conventional tidal volume ventilation and the subject method of distal delivery of tidal volume with perfusion of airway dead space. For this experiment, a 2.5 kg New Zealand white rabbit was anesthetized with 30 mg/kg pentobarbital, exsanguinated and the lungs removed from the chest. Each lung was degassed and filled with 8 ml of 5% bovine albumin in Kreb's solution labelled with 0.7 mg/ml of Evans Blue dye. Each lung was separately ventilated with unlabelled 5% albumin solution while clamping the mainstem bronchus to the opposite lung. The right lung was ventilated with 1.5 ml tidal volume through a cannulae tied in the trachea and each expired tidal volume collected in a test tube (conventional tidal volume ventilation) and optical density read at 620 nm on a spectrophotometer. The left lung was ventilated by infusing the 1.5 ml tidal volume through a small bore catheter placed into the distal airways and removing the expired tidal volume by a separate catheter in the trachea. Tidal volumes were collected for optical density measurements. An additional volume of 0.2 ml was infused at end-inspiration and at end-expiration while simultaneously withdrawing an equal amount at the trachea to maintain a constant lung volume. The blue color of the perfusate removed in these isovolumetric states indicated that removal of labelled alveolar liquid continued in the isovolumetric states.

Optical density of Evans blue dye labelled albumin read at 620 nm, as a function of the number of breaths using conventional tidal liquid (closed circles) and distal-perfused tidal liquid (closed squares) ventilation in normal rabbit lungs is shown in FIG. 3. The combination of distal airway delivery of unlabelled albumin solution and isovolumetric perfusion of the airway dead space resulted in a rate constant (k) for clearance of labelled albumin which was over twice that for tidal ventilation alone even though the total ventilations were exactly equal for both modes of ventilation. While the experimental data shown here represents convective and diffusive removal of a solute (albumin) with a diffusion rate that differs from that of respiratory gases in perfluorocarbon liquid, the effects of the two modes of ventilation should be qualitatively similar for removal of respiratory $CO_2$.

EXAMPLE IV

Animal preparation and measurements. Heart worm negative, mongrel dogs (15–20 kg) are anesthetized with 30 mg/kg sodium pentobarbital, intubated and mechanically ventilated on room air (Healthdyne). The right femoral artery and vein and right jugular vein are cannulated. Systemic arterial pressure (Psa) is monitored and arterial blood gas samples are removed through the femoral artery and drugs and solutions infused via the femoral vein. A balloon tipped thermal dilution catheter is introduced through the jugular vein to monitor pulmonary artery pressure (Ppa). Psa and airway pressure (Paw) are monitored and recorded using a DATAQ data acquisition system (DATAQ Inst. Co., Akron, Ohio), digital computer (Gateway), and printer. Animals are paralyzed using 0.1 mg/kg Pancuronium bromide and measurements of helium dilution functional residual capacity (FRC) (Equilibrated Biosensors Helium FRC machine), lung compliance and airway resistance are performed (Bicord pulmonary function computer). Arterial $PO_2$, $PCO_2$, pH, hemoglobin saturation and hematocrit are measured initially and at intervals throughout the experiments (Radiometer ABL5 Blood Gas and OSM3 Hemoximeter machines).

To initiate liquid ventilation, animals are ventilated with 100% $O_2$ for 15 minutes and either a standard, cuffed endotracheal tube or the specially constructed bronchial tube are introduced down the trachea. The lungs are filled with Rimar 101 perfluorocarbon liquid (Mitani, Milan, Italy) to 25% above FRC to enhance expiratory liquid flow rates (Schoenfish and Kylstra 1973). Nominal liquid ventilation is started and parameters adjusted to reach isocapnea. A flow of 10 l/min $O_2$ through the membrane oxygenator is used and equilibration confirmed by sampling outflow PFC liquid. Bicarbonate is infused I.V. if arterial pH falls to 7.25. Lung compliance in the liquid filled lung is monitored using expired liquid volume and the change airway pressure, i.e., (flow×time)/ΔPaw.

For each mode of ventilation, the maximal $O_2$ uptake ($VO_2$) and $CO_2$ elimination rates ($VCO_2$) are determined as a function of respiratory rate according to Koen et al. (1988). $CO_2$ elimination rate equals integrated expiratory flow× $PCO_2$×solubility in PFC liquid; and $O_2$ uptake rate equals inspiratory flow×$PO_2$ solubility—expiratory flow ×$PO_2$× solubility. The theoretical upper limit for improvement in gas exchange by converting dead space ventilation to alveolar ventilation equals the dead space fraction of tidal volume plus any convective and diffusive exchange during isovolumetric perfusion. Dead space fraction is equal to 30% in normal lungs, but may exceed 70% in certain types of lung disease (Taylor et al. 1989).

The following physiologic variables are also calculated in each experiment: pulmonary vascular resistance from Ppa, pulmonary wedge pressure and cardiac output, alveolar to arterial $PO_2$ gradient and pulmonary shunt fraction from blood gases and inspired $PO_2$ using standard formulas (Taylor et al. 1989). Alveolar liquid pressure is also determined periodically from Paw by stopping both pumps for 3 seconds at end-inspiration and end-expiration (Curtis et al. 1990).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Adkins, W. K., et al. *Crit. Care Med.* 19(3):390–393, 1991.
Bachofen, M., et al. In: *Pulmonary Edema. Clinical Physiology Series*, Eds. A. P. Fishman, and E. M. Rankin, Bethesda, Md., American Physiological Society, pp. 241–252, 1979
Cadenas, M., et al. *J. Pediatr. Surg.* 30:1178–1182, 1995
Coker, P. J., et al. *Crit. Care Med.* 20:635–640, 1992
Curtis, S. E., et al. *J. Appl. Physiol.* 68:2322–2328, 1990
Egan, E. A., et al. *J. Physiol.* (Lond) 260:409–424, 1976
Freeman, B. A., and J. D. Crapo. *Lab Invest.* 47:412–426, 1982
Gil, J. H., et al. *J. Appl. Physiol.* 47:990–1001, 1979
Greenfield, L. J., et al. *Anesthesiology* 25:312–316, 1964
Greenspan, J. S., et al. *Lancet* 2:1095, 1989
Greenspan, J. S., et al. *J. Pediatr.* 117:106–111, 1990
Hernandez, L. A., et al. *J. Appl. Physiol.* 66(5):2364–2368, 1989
Hernandez, L. A., et al. *J. Appl. Physiol.* 69:2057–2061, 1990
Hirschl, R. B., et al. *J. Pediatr. Surg.* 28:513–518, 1993
Hirschl, R. B., et al. *Artif. Cells Blood Substit. Immobil. Biotechnol.* 22:1389–1396, 1994a
Hirschl R. B. et al *Surgery* 116:159–167, 1994b
Hirschl R. B. et al *Crit. Care Med.* 23:157–163, 1995a
Hirschl R. B. et al *Lancet* 346:1201–1202, 1995b
Hirschl R. B. et al *Chest* 108:500–508, 1995c
Hirschl R. B. et al *Ann. Surg.* 221:79–88, 1995d
Jackson J. C. et al *Artif. Cells Blood Substit. Immobil. Biotechnol.* 22:1121–1132, 1994
Jobe, A., et al. *J. Appl. Physiol.* 55:169–176, 1983
Jobe, A., et al. *J. Appl. Physiol.* 58:1246–1251, 1985
Jobe, A., and M. Ikegami. *Am. Rev. Respir. Dis.* 136:1256–1275, 1987
Koen, P. A., et al. *Pediatric Res.* 24:291–296, 1988
Leach, C. L., et al. *J. Pediatr.* 126:412–420, 1995
Lowe, C. A., and T. H. Shaffer. *J. Appl. Physiol.* 60:154–159, 1986
Moskowitz, G. D., et al. *Medical Instrumentation* 5:273–278, 1971
Nesti, F. D., et al. *Crit. Care Med.* 22:1445–1452, 1994
Northway Jr., W. H., et al. *New Engl. J. Med.* 276:357–368, 1967
Obrodovich, H. M., and Mellins, R. B. *Am. Rev. Respir. Dis.* 132:694–709, 1985
Parker, J. C., et al. *J. Appl. Physiol.* 57:1809–1816, 1984
Parker, J. C., et al. *Am. Rev. Respir. Dis.* 142:321–328, 1990
Parker, J. C. *Crit. Care Med.* 21:131–143, 1993
Petty, T. L., and D. G. Ashbaugh. *Chest* 60:233–239, 1971
Pingleton, S. K. *Am. Rev. Respir. Dis.* 137:1463–1493, 1988
Schoenfish, W. H., and J. A. Kylstra. *J. Appl. Physiol.* 35:117–121, 1973
Seeger, W., et al. *J. Appl. Physiol.* 58:326–338, 1985
Sekins, K. M., et al. *Artif. Cells Blood Substit. Immobil. Biotechnol.* 22:1381–1387, 1994
Shaffer, T. H., and G. D. Moskowitz. *J. Appl. Physiol.* 36:208–213, 1974
Shaffer, T. H., et al. *Pediatr. Res.* 17:680–668, 1983
Shaffer, T. H., et al. *Pediatr. Res.* 18:47–52, 1984
Shaffer, T. H., et al. In: *New Therapies for Neonatal-Respiratory Failure: A Physiologic Approach*, Eds. B. R. Boynton, W. A. Carlo, A. H. Jobe. Cambridge Univ. Press, Cambridge, UK, 1994
Smith, T. M., et al. *Crit. Care Med.* 23:1533–1539, 1995
Taylor, A. E., et al. *Clinical Respiratory Physiology*, W. B. Saunders, Co., Philadelphia, Pa. 1989
Thomas, S., et al. *J. Comput. Assist. Tomogr.* 10:1–9, 1986
Webb, H. H., and D. F. Tierney. *Am. Rev. Respit. Dis.* 110:556–565, 1974
Wolfson, M. R., et al. *J. Appl. Physiol.* 72:1024–1031, 1992
Woodring, J. H. *Crit. Care Med.* 13:786–791, 1985

What is claimed is:

1. A liquid ventilator comprising:

a source of oxygenated liquid;

an inspiratory conduit having a first end connected to said source of oxygenated liquid and a second end;

a bifurcated bronchial tube connected to the second end of said inspiratory conduit, said bifurcated bronchial tube having a left lumen for directing the flow of oxygenated liquid into a left primary bronchus of a subject and a right lumen for directing the flow of oxygenated liquid into a right primary bronchus of said subject; and a pump for pumping said oxygenated liquid from said source through said inspiratory conduit and said bifurcated bronchial tube to said left primary bronchus and said right primary bronchus.

2. The liquid ventilator of claim 1 wherein said source of oxygenated liquid comprises a liquid reservoir connected to a membrane oxygenator for diffusing oxygen through liquid removed from said reservoir.

3. The liquid ventilator of claim 1 wherein said liquid ventilator further comprises a heat exchanger for warming said oxygenated liquid.

4. The liquid ventilator of claim 1 wherein said liquid ventilator further comprises a computer for controlling the flow of oxygenated liquid from said source to said bifurcated bronchial tube.

5. The liquid ventilator of claim 1 wherein said oxygenated liquid comprises perfluorocarbon.

6. The liquid ventilator of claim 1 wherein said liquid ventilator further comprises a pressure transducer to sense liquid pressure at said right primary bronchi and said left primary bronchi.

7. The liquid ventilator of claim 6 wherein said liquid ventilator further comprises a computer, and wherein said pressure transducer sends signals to said computer based on said liquid pressure.

8. The liquid ventilator of claim 1 wherein said liquid ventilator further comprises an outflow pump for removing deoxygenated liquid from said subject.

9. The liquid ventilator of claim 1 wherein said bifurcated bronchial tube is a double lumen tube.

10. A method for liquid ventilation of a subject, said method comprising:

inserting a bifurcated bronchial tube into a subject, said bifurcated bronchial tube having a left lumen for directing the flow of oxygenated liquid into a left primary bronchus of said subject and a right lumen for directing the flow of oxygenated liquid into a right primary bronchus of said subject; and providing a flow of oxygenated liquid into said bifurcated bronchial tuber thereby ventilating said subject with said oxygenated liquid.

11. The method of claim 10 wherein at least a portion of said flow of oxygenated liquid is provided continuously throughout said liquid ventilating in an isovolumetric manner.

* * * * *